United States Patent [19]

Asakura et al.

[11] Patent Number: 5,781,288
[45] Date of Patent: Jul. 14, 1998

[54] METHOD OF INSPECTING LOCATION OF OPTICAL FILM AND SYSTEM FOR CARRYING OUT THE METHOD

[75] Inventors: Motoh Asakura; Kazuya Kobayashi, both of Matsusaka; Shinji Nishikawa, Ise, all of Japan

[73] Assignee: Central Glass Company, Limited, Yamaguchi, Japan

[21] Appl. No.: 719,373

[22] Filed: Sep. 25, 1996

[30]    Foreign Application Priority Data

| Sep. 27, 1995 | [JP] | Japan | 7-249287 |
| Jun. 26, 1996 | [JP] | Japan | 8-166435 |
| Jul. 29, 1996 | [JP] | Japan | 8-198879 |

[51] Int. Cl.$^6$ ........................................ G01N 21/00
[52] U.S. Cl. ........................................ 356/239; 348/86
[58] Field of Search ........................ 356/239, 381, 356/375, 376, 237, 240, 430, 431, 243, 251, 252, 253, 254; 250/559.29, 559.27, 559.28, 559.22, 559.19; 348/86, 91, 92, 94, 95, 96, 125, 129, 130, 131

[56]          References Cited

U.S. PATENT DOCUMENTS 3,187,185  6/1965  Milnes ........................... 356/381
5,343,288  8/1994  Cohen et al. ................... 356/239

*Primary Examiner*—K. Hantis
*Attorney, Agent, or Firm*—Evenson, McKeown, Edwards & Lenahan, PLLC

[57]          ABSTRACT

A method of inspecting the location of a polarization-direction changing film relative to a transparent plate at a predetermined position. The method comprises the following steps: (a) disposing a first polarizing plate to face a first surface of the transparent plate and at a standard position at which the first polarizing plate has inner and outer peripheries, in section, defining therebetween an area corresponding to a permissible range for location of a peripheral edge of the polarization-direction changing film; (b) disposing a second polarizing plate to face a second surface of the transparent plate, in which the polarization-direction changing film is located relative to the transparent plate; and (c) observing a locational relationship between the peripheral edge of the polarization-direction changing film and the area of the first polarizing plate through the second polarizing plate so as to make a judgment as to whether the peripheral edge of the. polarization-direction changing film is within the allowable range.

14 Claims, 7 Drawing Sheets

5,781,288

METHOD OF INSPECTING LOCATION OF OPTICAL FILM AND SYSTEM FOR CARRYING OUT THE METHOD

BACKGROUND OF THE INVENTION

1. Field of the Invention

This invention relates to improvements in method and system for inspecting the location of an optical film (such as a polarization-direction changing film or a hologram) relative to a transparent plate for the purpose of judging as to whether the optical film is located within a permissible range relative to the transparent plate, the method and system being applicable to method and system for automatically sticking the optical film on the transparent plate with the permissible range.

2. Description of the Prior Art

Hitherto head-up display systems have been proposed and put into practical use in the field of vehicles for the purpose of, for example, projecting a variety of vehicle operating information onto a front windshield glass. One of the head-up display systems includes a polarization-direction (plane) changing film which is usually stuck on one of laminated plate glasses and located between the plate glasses in order to prevent a double image from forming at the front windshield glass. Another one includes a hologram which is stuck on a front windshield glass in order to reconstruct thereon the vehicle operating information.

In case of using the polarization-direction changing film, a double image tends to be formed on the front windshield glass and observed by a driver unless the film is stuck precisely at a predetermined position. This is not desirable from the view point of safety. In case of using the hologram, an optical deviation is unavoidably made between the hologram and a light source for reconstruction thereby failing an effective use of light unless the hologram is stuck precisely at a predetermined position.

In view of the above, it is required to inspect as to whether the polarization-direction changing film or hologram is stuck precisely at the predetermined position or not. Such inspection has been made, for example, by measuring the distance of the film or hologram from the edge of the windshield glass thereby judging the location of the film or hologram is accepted or rejected.

However, each of the polarization-direction changing film or the hologram is nearly colorless and transparent (though slightly colored), and the windshield glass is also transparent. As a result, it is difficult to detect the peripheral edge of the film or the hologram in the above conventional inspection, and therefore a long time is required to accomplish the inspection. A tendency of such difficulty is predominant particularly in case that the windshield glass is three-dimensionally curved like an automotive front windshield glass.

SUMMARY OF THE INVENTION

It is an object of the present invention to provide improved method and system for inspecting the location of an optical film (such as a polarization-direction changing film, or a hologram) relative to a transparent plate, which effectively overcome drawbacks encountered in conventional methods and systems.

Another object of the present invention is to provide improved method and system for inspecting the location of an optical film (such as polarization-direction changing film, or a hologram) relative to a transparent plate, by which detection of the peripheral edge of the optical film can be facilitated while making it possible easily and within a short time to inspect as to whether the optical film is located at a permissible range or not relative to the surface of the transparent plate.

A further object of the present invention is to provide improved method and system for sticking an optical film (such as polarization-direction changing film) on a transparent plate, by which the optical film can be automatically stuck on the surface of the transparent plate within a permissible range of a standard position.

A first aspect of the present invention resides in a method of inspecting a location of an optical film relative to a transparent plate at a predetermined position. The method comprises the following steps: (a) disposing an inspection plate to face a surface of the transparent plate and at a standard position at which the inspection plate includes an optically functioning section which has inner and outer peripheries, in section, defining therebetween an area corresponding to a permissible range for location of a peripheral edge of the optical film; and (b) observing a locational relationship between the peripheral edge of the optical film and the area of the inspection plate under action of light reaching the optically functioning section so as to make a judgment as to whether the peripheral edge of the optical film is within the allowable range.

A second aspect of the present invention resides in a system for inspecting a location of an optical film relative to a transparent plate. The system comprises mount means for supporting the transparent plate in conformity with a curvature of the transparent plate, the mount means including stoppers for locating the transparent plate. An inspection plate is disposed facing a surface of the transparent plate and located at a standard position at which the inspection plate includes an optically functioning section which has inner and outer peripheries, in section, defining therebetween an area corresponding to a permissible range for location of a peripheral edge of the optical film. Additionally, a light source is provided to emit light to reach the optically functioning section and the optical film, the optical film being located relative to a surface of the transparent plate.

A third aspect of the present invention resides in a method of inspecting a location of a polarization-direction changing film relative to a transparent plate at a predetermined position. The method comprises the following steps: (a) disposing a first polarizing plate to face a first surface of the transparent plate and at a standard position at which the first polarizing plate has inner and outer peripheries, in section, defining therebetween an area corresponding to a permissible range for location of a peripheral edge of the polarization-direction changing film; (b) disposing a second polarizing plate to face a second surface of the transparent plate, in which the polarization-direction changing film is located relative to the transparent plate; and (c) observing a locational relationship between the peripheral edge of the polarization-direction changing film and the area of the first polarizing plate through the second polarizing plate so as to make a judgment as to whether the peripheral edge of the polarization-direction changing film is within the allowable range.

A fourth aspect of the present invention resides in a system for inspecting a location of a polarization-direction changing film relative to a transparent plate. The system comprises mount means for supporting the transparent plate in conformity with a curvature of the transparent plate, the mount means including stoppers for locating the transparent plate. A first polarizing plate is disposed facing a first surface of the transparent plate and located at a standard position at which the first polarizing plate has inner and outer peripheries, in section, defining therebetween an area corresponding to a permissible range for location of a peripheral edge of the polarization-direction changing film. A second polarizing plate is disposed facing a second surface of the transparent plate, the polarization-direction changing film being located relative to the transparent plate. Additionally, a light source is disposed facing the first surface of the transparent plate and located such that the first polarizing plate is positioned between the light source and the transparent plate.

A fifth aspect of the present invention resides in a method of sticking a polarization-direction changing film on a transparent plate at a predetermined position. The method comprises the following steps: (a) disposing a first polarizing plate to face a first surface of the transparent plate and at a standard position at which the first polarizing plate has inner and outer peripheries, in section, defining therebetween an area corresponding to a permissible range for location of a peripheral edge of the polarization-direction changing film; (b) disposing a second polarizing plate to face a second surface of the transparent plate, in which the polarization-direction changing film is located relative to the transparent plate; (c) moving the polarization-direction changing film toward a predetermined position corresponding to the standard position; (d) observing a locational relationship between the peripheral edge of the polarization-direction changing film and the area of the first polarizing plate through the second polarizing plate so as to make a judgment that the peripheral edge of the polarization-direction changing film is within the allowable range; and (e) sticking the polarization-direction changing film on the second surface of the transparent plate at the standard position in response to the judgment.

A sixth aspect of the present invention resides in a system for sticking a polarization-direction changing film on a transparent plate at a standard position. The system comprises a first polarizing plate disposed facing a first surface of the transparent plate and at a standard position at which the first polarizing plate has inner and outer peripheries, in section, defining therebetween an area corresponding to a permissible range for location of a peripheral edge of the polarization-direction changing film. A second polarizing plate is disposed facing a second surface of the transparent plate, the polarization-direction changing film being located relative to the transparent plate. Means is provided to move the polarization-direction changing film toward a predetermined position corresponding to the standard position. Means is provided to observe a locational relationship between the peripheral edge of the polarization-direction changing film and the area of the first polarizing plate through the second polarizing plate so as to make a judgment that the peripheral edge of the polarization-direction changing film is within the allowable range. Additionally, means is provided to stick the polarization-direction changing film on the second surface of the transparent plate at the standard position in response to the judgment.

A seventh aspect of the present invention resides in a method of inspecting a location of a hologram relative to a transparent plate at a predetermined position. The method comprises the following steps: (a) disposing an inspection plate to face a surface of the transparent plate and at a standard position at which the inspection plate includes a light-interrupting section which has inner and outer peripheries, in section, defining therebetween an area corresponding to a permissible range for location of a peripheral edge of the hologram, and a light-passing section other than the light-interrupting section; (b) radiating light from a light source onto the hologram through the area of the inspection plate, in which the hologram is located relative to a surface of the transparent plate; and (c) observing a locational relationship between the peripheral edge of the hologram and the area of the inspection plate under action of light reaching the hologram upon passing through the light-passing section so as to make a judgment as to whether the peripheral edge of the hologram is within the allowable range.

An eighth aspect of the present invention resides in a method of inspecting a location of a hologram relative to a transparent plate at a predetermined position. The method comprises the following steps: (a) disposing an inspection plate to face a surface of the transparent plate and at a standard position at which the inspection a plate includes a light-passing section which has inner and outer peripheries, in section, defining therebetween an area corresponding to a permissible range for location of a peripheral edge of the hologram, and a light-interrupting section other than the light-passing section; (b) radiating light from a light source onto the hologram through the area of the inspection plate, in which the hologram is located relative to a surface of the transparent plate; and (c) observing a locational relationship between the peripheral edge of the hologram and the area of the inspection plate under action of light reaching the hologram upon passing through the light-passing section so as to make a judgment as to whether the peripheral edge of the hologram is within the allowable range.

A ninth aspect of the present invention resides in a system for inspecting a location of a hologram relative to a transparent plate. The system comprises mount means for supporting the transparent plate in conformity with a curvature of the transparent plate, the mount means including stoppers for locating the transparent plate. An inspection plate is disposed facing a surface of the transparent plate and located at a standard position at which the inspection plate includes an optically functioning section which has inner and outer peripheries, in section, defining therebetween an area corresponding to a permissible range for location of a peripheral edge of the hologram. Additionally, a light source is provided to emit light to reach the optically functioning section and the hologram, the hologram being located relative to a surface of the transparent plate.

According the above aspects of the present invention, detection of the edge of the optical film (such as a polarization-direction changing film or a hologram) can be easily accomplished, while making it possible easily and within a short time to judge as to whether the optical film is located within the permissible range relative to the transparent plate. Such inspection and judgment have been difficult to be accomplished with conventional similar methods and systems. Additionally, by applying the above method and system to method and system for sticking the optical film onto the transparent plate, it can be accomplished to automatically stick the optical film on the transparent plate precisely within the allowable range.

BRIEF DESCRIPTION OF THE DRAWINGS

In the drawings, like reference numerals designate like parts and elements throughout all figures, in which.

DETAILED DESCRIPTION OF INVENTION

Figure 1:
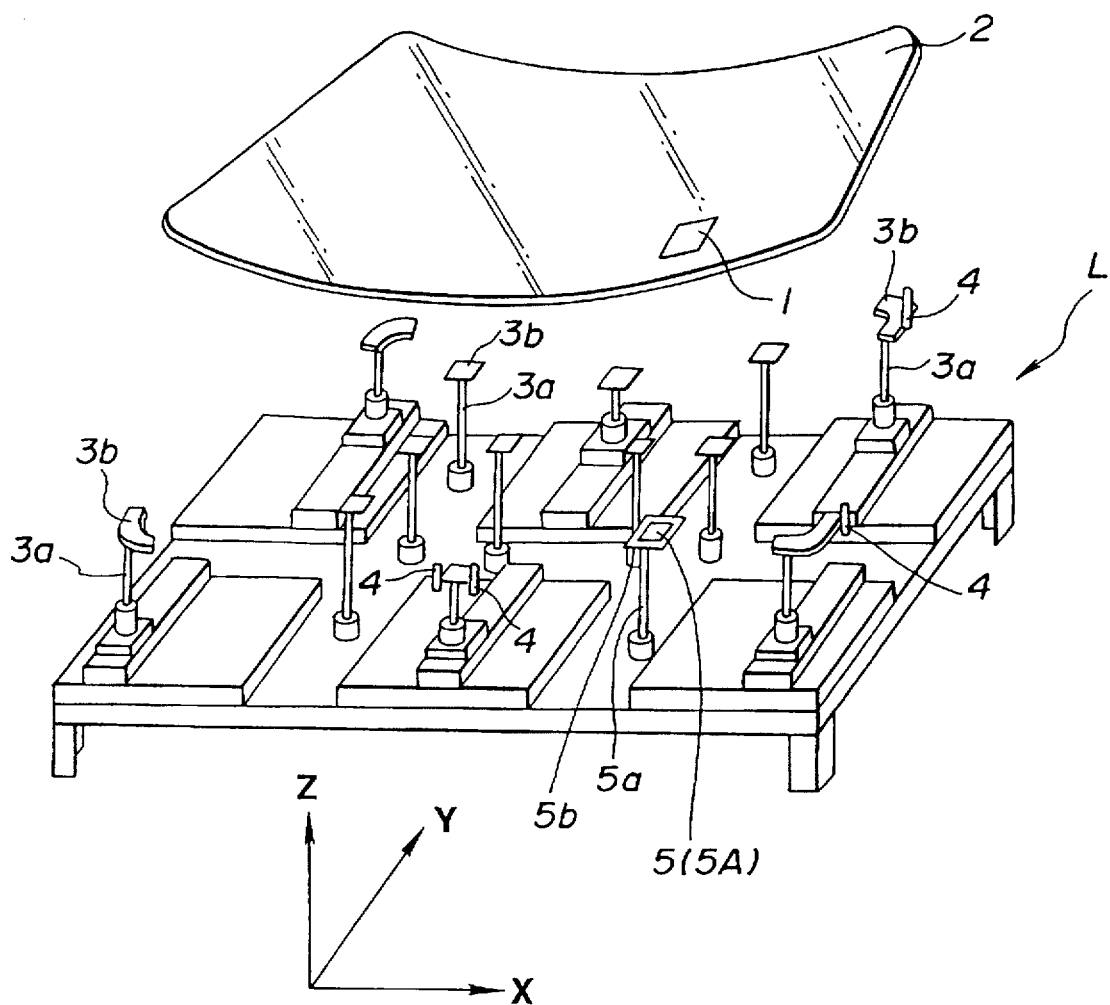
FIG. 1 is a perspective view of an essential part of a first embodiment of a system for inspecting the location of an optical film, according to the present invention.

Referring now to FIGS. 1 to 5, a first embodiment of a location inspecting system according to the present invention is illustrated by the reference numeral L. The location judging system L of this embodiment is for judging the location of a polarization-changing film 1 relative to a front windshield glass of an automotive vehicle.

The polarization-direction changing film 1 of this embodiment is a liquid crystal high polymer which is in twisted nematic orientation under a liquid crystal condition and is in a glassy state at a temperature lower than a liquid crystal transition point thereof. The polarization-direction changing film functions to change or adjust the direction (plane) of polarization of rays of light to be incident thereon.

The polarization-direction changing film 1 is stuck on the concave surface of an outboard-side transparent (glass) plate 2 of the front windshield glass with an adhesive tape (not shown). The outboard-side transparent plate is curved in which the polarization-changing film 1 is stuck on the concave surface of the transparent plate 2. Thereafter, an inboard-side transparent (glass) plate (not shown) is stuck to the outboard-side transparent plate 2 with an intermediate film (not shown) which is formed of polyvinyl butyral or the like and located between the outboard-side transparent plate 1 and the inboard-side transparent plate. Then, a usual autoclave treatment is conducted on the above glass arrangement including the outboard-side and inboard-side transparent plates thereby accomplishing a laminating process thus forming the front windshield glass.

Figure 3:
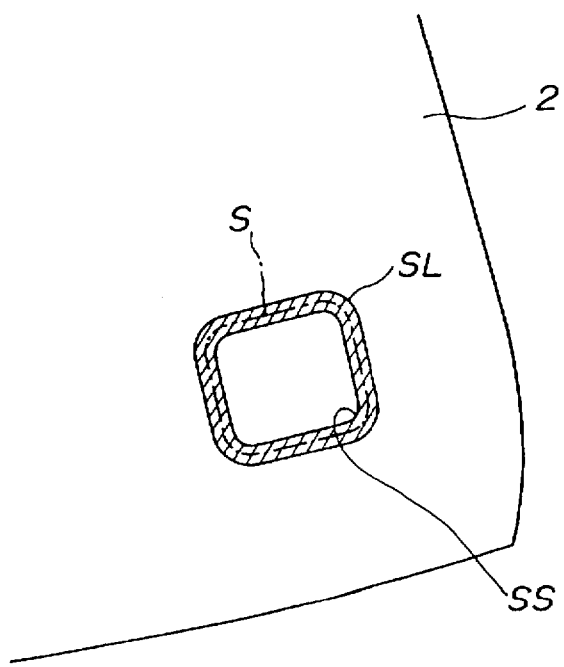
FIG. 3 is a fragmentary plan view of a transparent plate, showing a locational relationship of an optical film relative to the transparent plate.

An inspection for location of the polarization-direction changing film 1 is accomplished before the above laminating process by using the location inspecting system L. The polarization-direction changing film 1 is to be located and stuck such that its peripheral edge is located at or brought into coincidence with a standard peripheral position S indicated by a dot-dash line in FIG. 3. However, in fact, it is difficult to accurately locate the polarization-direction changing film 1 at this standard position S, and therefore it is permitted that the peripheral edge of the polarization-direction changing film 1 is located between an outer permissible line SL and an inner permissible line SS as shown in FIG. 3. The outer permissible line SL is separate outward from the dot-dash line of the standard peripheral position S, for example, by 1 to several mm, while the inner permissible line SS is separate inward from the dot-dash line of the standard peripheral position S, for example, by 1 to several mm. It will be understood that the location of the stuck polarization-direction changing film 1 is judged to be suitable or accepted, in case that the polarization-direction changing film 1 is stuck such that the peripheral edge thereof is located between the outer permissible line SL and the inner permissible line SS.

As shown in FIG. 1, the location inspecting system L of this embodiment comprises a mount table 3 which is provided with a plurality of support rods 3a which vertically upward extend from the mount table 3. Each support rod 3a is arranged to be vertically extensible and contractible. A support mount 3b is attached to the tip end of each support rod 3a, in which the position of the support mount 3b is vertically movable so as to be brought into tight contact with the convex surface of the transparent plate 2 having a curvature.

In this embodiment, the six support mounts 3b located near the peripheral edge of the mount table 3 and arranged to be movable in horizontal (X- and Y-axes) directions and in a vertical (Z-axis) direction as shown in FIG. 1. Each support mount 3b is connected to the tip end of the support rod 3a through a universal joint so as to be pivotal in various directions. Accordingly, each support mount 3b can be brought into tight contact with the convex surface of the transparent plate 2 having the curvature. Each of the three support mounts 3b of the above six support mounts 3b is provided with a rod-like stopper or stoppers 4 with which the peripheral edge of the transparent plate 2 is to be contacted.

Figure 2:
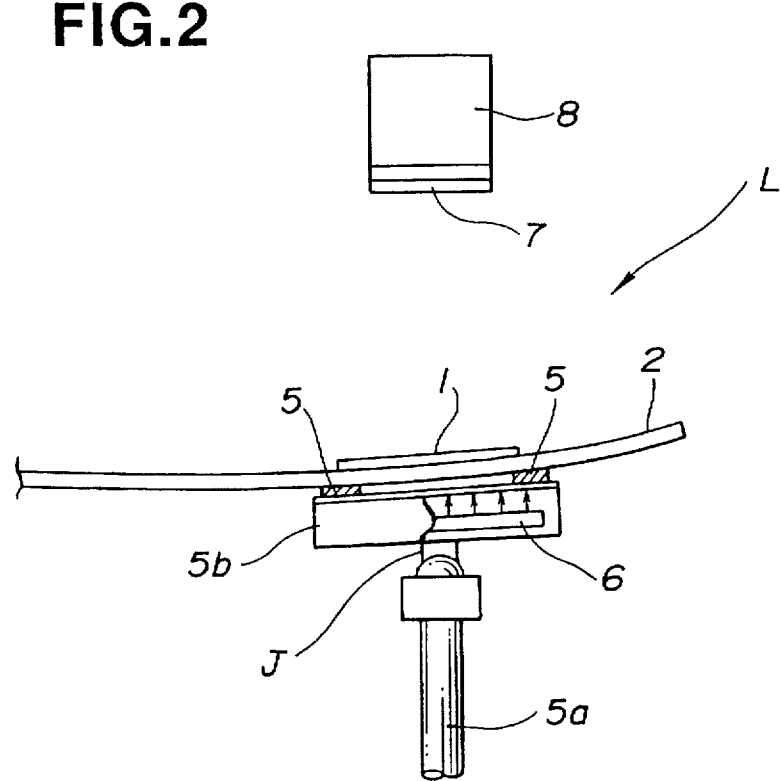
FIG. 2 is a fragmentary side view, partly in section, of an essential part of the system of FIG. 1.

A support rod 5a is provided extending vertically upwardly from the mount table 3 and arranged to be vertically extensible and contractible. As shown in FIG. 2, the support mount 5b is pivotally connected through a universal joint J to the tip end of the support rod 5a. A rectangular frame-shaped first polarizing plate or film 5 is disposed on the support mount 5b so as to polarize rays of light to be incident thereon. A light source 6 is disposed within the support mount 5b to emit light to the first polarizing plate 5. The first polarizing plate 5 is to be tightly contactable to the convex-side surface of the transparent plate 2 at a position corresponding to the polarization-direction changing film 1 stuck on the concave or opposite surface of the transparent plate 2 as shown in FIG. 2. The first polarizing plate 5 of this embodiment is formed by being cut out from a flat plate or film of a polarizing material in a manner to have the rectangular frame-shape. The rectangular frame-shaped polarizing plate 5 has a cross-sectional area which is the same in dimensions as an area (hatched area) defined between the solid lines SL and SS in FIG. 3. The first polarizing plate 5 is adhered on the surface of a transparent plate (not shown) such as a glass sheet or a sheet of polyethylene terephthalate.

As shown in FIG. 2, a second polarizing plate or film 7 is disposed over the polarization-direction changing film 1 and attached to the tip end section of a video camera 8. The second polarizing plate 7 functions to polarize rays of light which is from light source 6 and incident on the second polarizing plate 7. The second polarizing plate 7 has a direction (plane) of polarization which is parallel with or perpendicular to the direction of polarization of the first polarizing plate 7.

A manner of inspection for location of the polarization-direction changing film 1 using the location inspecting system L will be discussed hereinafter.

The transparent plate 2 (such as a glass plate) to which the polarization-direction changing film-1 has been stuck is mounted on the support mounts 3b before accomplishing the laminating process, in which the vertical dimension of respective support rods 3a are so adjusted that the support mounts 3b are brought into tight contact with the convex surface of the transparent plate 2 having the curvature. Then, the peripheral edges of the transparent plate 2 are brought into contact with the stopper or stoppers 4 at the three support mounts 3b so that the transparent plate 2 are mounted at a predetermined position. At this time, the first polarizing plate 5 is also adjusted in height or the like in conformity with the curvature of the transparent plate 2.

In this state, rays of light from the light source 6 are radiated to be incident on the first polarizing plate 5. Then, the rays of light are polarized and passed through the polarization-direction changing film 1 after passing through the transparent plate 2, in which the polarized rays of light are changed or optically rotated by 90 degrees in angle. The thus optically rotated rays of light are incident on the second polarizing plate 7.

Figure 4:
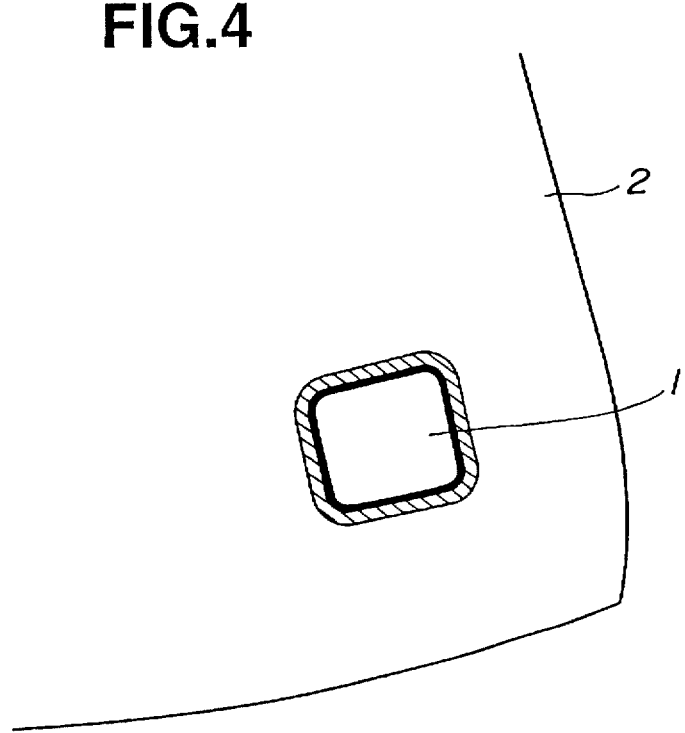
FIG. 4 is a fragmentary plan view similar to FIG. 3 but showing the locational relationship in an operational mode.

When an observation for the side of the polarization-direction changing film 1 is made from the upper side of the second polarizing plate 7 through the second polarizing plate 7, an optical image as shown in FIG. 4 is observed in case that the second polarizing plate 7 is arranged to have the direction (plane) of polarization parallel with that of the first polarizing plate 5. In FIG. 4, the rays of light passing through the first polarizing plate 5 (the hatched area in FIG. 3) and the polarization-direction changing film 5 are seen black (corresponding to a blackened area in FIG. 4), while the rays of light which pass through the first polarizing plate 5 (the hatched area in FIG. 3) and do not pass through the polarization-direction changing film 5 are seen gray (corresponding to a hatched area in FIG. 4). Other rays of light pass through only the transparent plate 2 and therefore are seen transparent.

Figure 5:
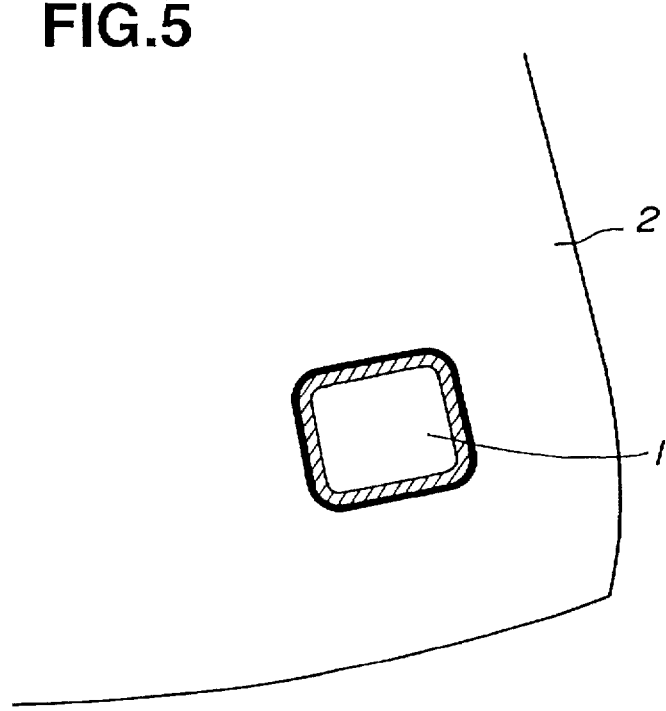
FIG. 5 is a fragmentary plan view similar to FIG. 3 but showing the locational relationship in another operational mode.

Otherwise, in case that the second polarizing plate 7 is arranged to have the direction (plane) of polarization perpendicular to that of the first polarizing plate 5, an optical image as shown in FIG. 5 is observed. In FIG. 5, the rays of light passing through the first polarizing plate 5 (the hatched area in FIG. 3) and the polarization-direction changing film 5 are seen gray (corresponding to a hatched area in FIG. 5), while the rays of light which pass through the first polarizing plate 5 (the hatched area in FIG. 3) and do not pass through the polarization-direction changing film 5 are seen black (corresponding to a blackened area in FIG. 5). Other rays of light pass through only the transparent plate 2 an therefore are seen transparent.

It is preferable that the second polarizing plate 7 is arranged to have the direction (plane) of polarization parallel with that of the first polarizing plate 5 because the rays of light passing through both the first polarizing plate 5 and the polarization-direction changing film 1 seen black or constitute the blackened area which can be most readily discriminated, in which the dimensions of the blackened area are measured to obtain a tendency of location of the polarization-direction changing film thereby making it possible to feedback the tendency to production processes before the inspection.

The optical image (as shown in FIG. 4 or 5) around the polarization-direction changing film 1 is picked up by the video camera 8 and subjected to an optical image processing in which the optical image having light and dark tones is processed by an image processing device (not shown). It will be understood that judgment is made as the location of the polarization-direction changing film 1 being accepted or within a permissible range if the blackened area and the hatched area (in FIG. 4 or 5) are contiguous with each other along their whole peripheral edge, whereas judgment is made as the location being rejected or not within the permissible range if the blacked area and the hatched area are separate even partially from each other.

While the polarization-direction changing film 1 of the above embodiment has been described as being formed of the liquid crystal high polymer which is in twisted nematic orientation under liquid crystal condition and is; in glassy state at a temperature lower than a liquid crystal transition point thereof, it will be understood that the polarization-direction changing film may be replaced with other polarization-direction changing films such as a so-called λ/2 film or plate which functions to optically rotate the direction (plane) of polarization of plane-polarized light. However, the polarization-direction changing film formed of the above-mentioned liquid crystal high polymer is preferable because it is high in transmissivity throughout a wide range of wavelengths.

Although the transparent plate 2 used in the above embodiment has been shown and described as being the curved front windshield glass of the automotive vehicle, it will be appreciated that the transparent plate may be a windshield glass of other vehicles such as an airplane. Additionally, the transparent plate 2 may be replaced with a transparent plate forming part of a combiner of a head-up display system which is disposed separate from a front windshield glass, in which the transparent plate is made of not only glass but also transparent plastic such as polycarbonate or acrylic resin.

In the above-discussed embodiment, the inspection of the location of the polarization-direction changing film 1 has been shown and described as being carried out before the laminating process. This is preferable from such a view point as to reuse the glass plate provided with the polarization-direction changing film which is stuck at a position out of the permissible range. However, such an inspection may be carried out after the laminating process.

Although the location inspecting system L of the embodiment has been shown and described as being arranged such that the length of each support rod 5a is variable in conformity with the curvature of the transparent plate 2, it will be understood that almost all constituent parts of the location inspecting system L may be formed to have a curved surface corresponding to the curvature of the transparent plate in case that transparent plates to be subjected to the inspection are generally constant in curvature.

While the second polarizing plate 7 has been shown and described as being attached to the tip end section of the video camera 8 so as to automatically inspect the location of the stuck polarization-direction changing film 1, it will be understood that the second polarizing plate 7 may be replace with polarizing glasses so that an operator makes the inspection.

Additionally, while the polarization-changing film 1 of the first embodiment has been shown and described as being used in a laminated glass, it will be understood that the polarization-changing film 1 may be stuck on a single plate glass.

Figure 6:
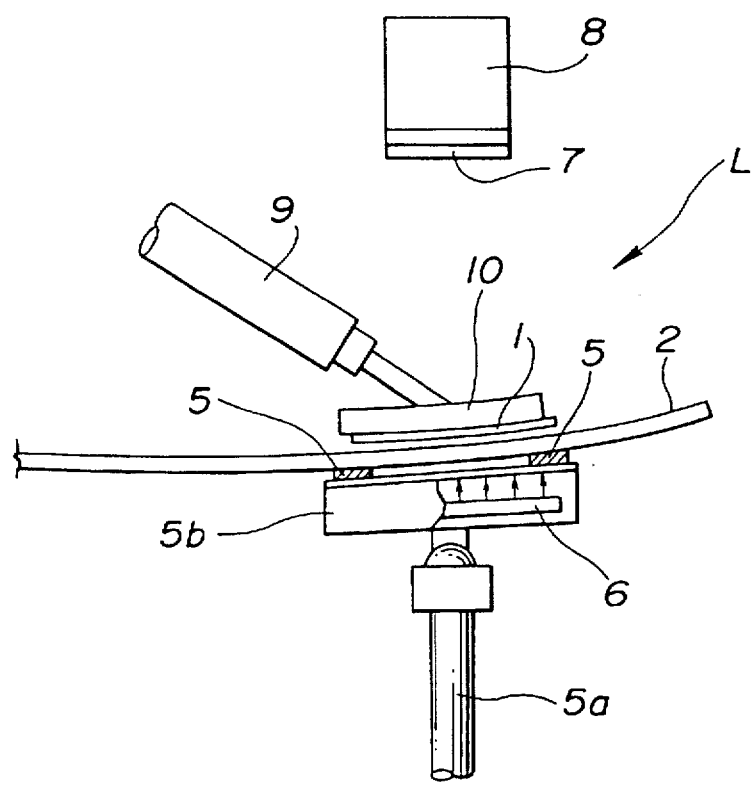
FIG. 6 is a fragmentary side view similar to FIG. 2 but showing an essential part of a second embodiment of the system according to the present invention;.
Figure 7:
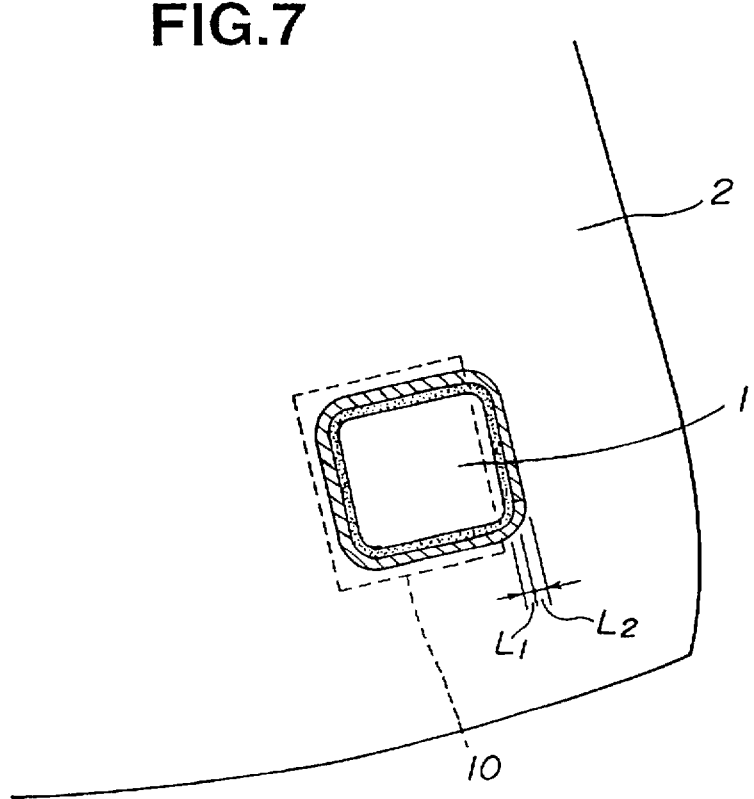
FIG. 7 is a fragmentary plan view of a transparent plate, showing a locational relationship of the optical film relative to the transparent plate in an operational mode, in the second embodiment.
Figure 8:
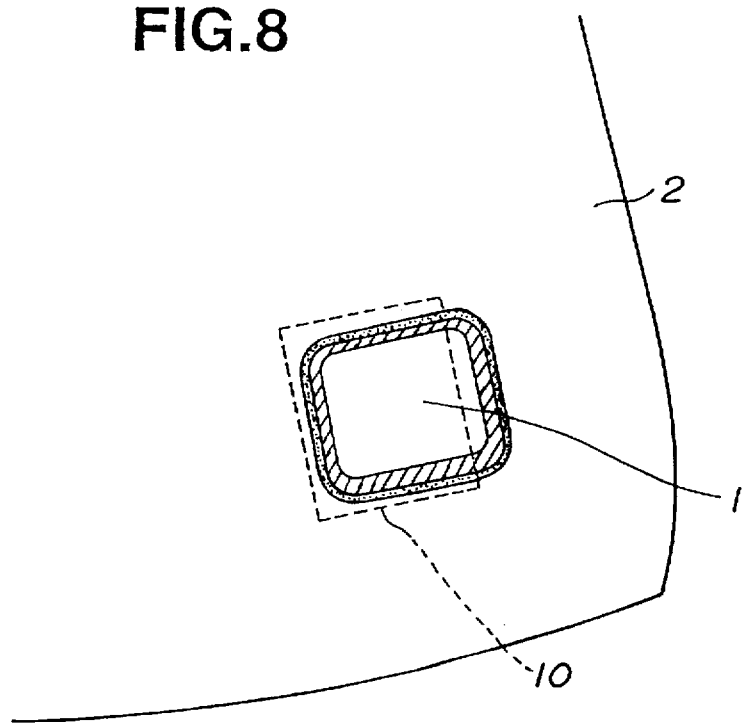
FIG. 8 is a fragmentary plan view similar to FIG. 3 but showing the locational relationship in an operational mode, in the second embodiment.

FIGS. 6 to 8 illustrate a second embodiment of the location inspecting system L according to the present invention, which is similar to the location judging system of the first embodiment. In this embodiment, the location inspecting system is incorporated in a sticking system S for automatically sticking the polarization-direction changing film 1 on the transparent plate 2 at a standard position corresponding to the position S in FIG. 3.

As shown in FIG. 6, the first and second polarizing plates 5, 7, the light source 6, the video camera 8 and the like are arranged in the same manner as that in the first embodiment shown in FIG. 2 and therefore form part of the location inspecting system L shown in FIG. 1. The transparent plate 2 is also located at the same position as that in the first embodiment shown in FIG. 2. In this embodiment, the sticking system S includes a robot arm 9 which is provided at its tip end with a suction plate 10. The robot arm 9 is constructed and arranged to be movable in the horizontal (X- and Y-axes) directions and in the vertical (Z-axis) direction as shown in FIG. 1. Additionally, the robot arm 9 includes two rotational shafts (not identified) by which the suction plate 10 is freely rotatable around the axis of the robot arm 9. The robot arm 9 is controllably driven under control of an image processing device (not shown). The suction plate 10 is formed at its suction (bottom) surface with a plurality of through-holes (not shown) which are in communication with a vacuum source (not shown). The suction plate 10 is arranged such that the through-holes thereof are controlled to take a vacuum condition or a non-vacuum condition.

The manner of operation of the sticking system S will be discussed also with reference to FIGS. 1 and 3.

The transparent plate 2 (such as a glass plate) is mounted on the support mounts 3b before accomplishing the laminating process, in which the vertical dimension of each support rods 3a is so adjusted that the support mounts 3b are brought into tight contact with the convex surface of the transparent plate 2 having the curvature. Then, the peripheral edges of the transparent plate 2 is brought into contact with the stopper or stoppers 4 at the three support mounts 3b so that the transparent plate 2 is mounted at a predetermined position. At this time, the first polarizing plate 5 is also adjusted in height or the like in conformity with the curvature of the transparent plate 2.

In this state, the suction plate 10 at the tip end of the robot arm 9 sucks and holds one of a plurality of polarization-direction changing films 1 which are cut to have a predetermined dimensions and put at a predetermined position. The thus held polarization-direction changing film 1 is moved to a predetermined position (shown in FIG. 6) under the action of the robot arm 9 which is controlled in accordance with the content of teaching which has been previously made to a controller (not shown) of the robot arm 9. The above predetermined position corresponds to the standard peripheral position S shown in FIG. 3 but upwardly separate by several mm from the concave surface of the transparent plate 2.

In this state, rays of light from the light source 6 are radiated to be incident on the first polarizing plate 5. The rays of light are polarized and passed through the polarization-direction changing film 1 after passing through the transparent plate 2, in which the polarized rays of light are changed or optically rotated by 90 degrees in angle. The thus optically rotated rays of light are incident on the second polarizing plate 7.

When an observation for the side of the polarization-direction changing film 1 is made from the upper side of the second polarizing plate 7 through the second polarizing plate 7, an optical image as shown in FIG. 7 is observed in case that the second polarizing plate 7 is arranged to have the direction (plane) of polarization parallel with that of the first polarizing plate 5. In FIG. 7, the rays of light passing through the first polarizing plate 5 (the hatched area in FIG. 3) and the polarization-direction changing film 5 is seen black (corresponding to a blackened area in FIG. 7), while the rays of light which pass through the first polarizing plate 5 (the hatched area in FIG. 3) and do not pass through the polarization-direction changing film 5 are seen gray (corresponding to a hatched area in FIG. 7). In case that the suction plate 10 is smaller in peripheral size than the polarization-direction changing film 5 so that four side sections of the film 5 project over the peripheral edge of the suction plate 10, the optical image as seen from the upper side of the second polarizing plate 7 is one shown in FIG. 7. In case that the suction plate is larger in peripheral size than the polarization-direction changing film 5 as indicated by a dotted line in FIG. 7, only one side section of the polarization-direction changing film 5 projects over the peripheral edge of the suction plate 10. Other rays which pass through only the transparent plate 2 are seen transparent.

Otherwise, in case that the second polarizing plate 7 is arranged to have the direction (plane) of polarization perpendicular to that of the first polarizing plate 5, an optical image as shown in FIG. 8 is observed. In FIG. 8, the rays of light passing through the first polarizing plate 5 (the hatched area in FIG. 3) and the polarization-direction changing film 5 are seen gray (corresponding to a hatched area in FIG. 8), while the rays of light which pass through the first polarizing plate 5 (the hatched area in FIG. 3) and do not pass through the polarization-direction changing film 5 are seen black (corresponding to a blackened area in FIG. 8). Other rays of light pass through only the transparent plate 2 and therefore are seen transparent.

The optical image (as shown in FIG. 7 or 8) around the polarization-direction changing film 1 is picked up by the video camera 8 and subjected to an optical image processing in which the optical image having light and dark tones is processed by an image processing device (not shown). It will be understood that judgment is made such that the location of the polarization-direction changing film 1 is accepted or within a permissible range if the blackened area and the hatched area (in FIG. 4 or 5) are contiguous with each other along their whole peripheral edge, whereas judgment is made such that the location is rejected or not within the permissible range if the blacked area and the hatched area are separate even partially from each other.

In the case that only one side section of the polarization-direction changing film 1 projects over the suction plate 10 as shown in FIG. 6, the locational relationship between the polarization-direction changing film 1 and the suction plate 10 are shown in FIG. 7 or 8. In this condition, in case of FIG. 7, the width L1 of the blackened or black area and the width L2 of the hatched or gray area are measured generally in one side section. The location of the suction plate 10 is corrected in case of L1≠L2 or in case of L1=L2 at a part while L1≠L2 at other parts so that the location of the polarization-direction changing film 1 is shifted inclined. Such correction of location of the suction plate 10 is carried out as follows:

A signal (not shown) from the video camera is output to the image processing device (not shown) which calculates a deviation or the like between the predetermined position and the actual position of the polarization-direction changing film 1 and outputs a correction signal (not shown) in accordance with the deviation or the like. The correction of the location of the polarization-direction changing film 1 is made in accordance with correction signal.

When such confirmation that the polarization-direction changing film 1 is located at the predetermined position is made, the suction plate 10 is moved downward so that the polarization-direction changing film 1 is brought into contact with the concave surface of the transparent plate 2. Then, the suction plate 10 is released from the vacuum condition. Thereafter, the polarization-direction changing film 1 is pressed on the transparent plate 2 from the side section projected from the suction plate 10 by a roll or the like thereby completely sticking the polarization-direction changing film 1 on the transparent plate 2. Thus, the polarization-direction changing film 1 can be quickly stuck on the surface of the transparent plate 2 by repeating the above operations.

In case that the suction plate 10 is smaller in peripheral size than the polarization-direction changing film 5 so that four side sections of the film 5 project over the peripheral edge of the suction plate 10, the location of the polarization-direction changing film 1 is accepted or within a predetermined range when the gray area and the black area are continuous with no break. At this time, the polarization-direction changing film 1 is stuck as it is onto the surface of the transparent plate 2. When the gray area and the black area are not continuous with a break(s), the location of the polarization-direction changing film 1 is corrected under the action of the image processing device, upon which the film 1 is stuck onto the surface of the transparent plate 2.

While judgment as to whether the polarization-direction changing film 1 is located at the predetermined position or not has been shown and described as being made by the video camera 8 and the image processing device in this embodiment, it will be understood that the second polarizing plate 7 is located slightly below the eyes of the operator when the judgment is made under observation of the operator's eyes. Additionally, in case of using a CCD camera (not shown) to make such judgment, the second polarizing plate 7 is disposed in front of the CCD camera.

Although sticking the polarization-direction changing film 1 has been shown and described as being accomplished under the action of the robot arm 9 and the like, it will be understood that the polarization-direction changing film 1 may be manually stuck on the transparent plate 2 by the operator.

The locational relationship between the polarization-direction changing film 1 and the suction plate 10 are such that at least one side section projects over the peripheral edge of the suction plate 10.

Accordingly, if the bottom surface (suction surface) of the suction plate 10 is flat, the projecting side section of the polarization-direction changing film 1 may hang down. In view of this, the lower surface of the suction plate 10 may be formed concave or convex with a small curvature to suppress the hanging-down of the film 1.

Figure 9:
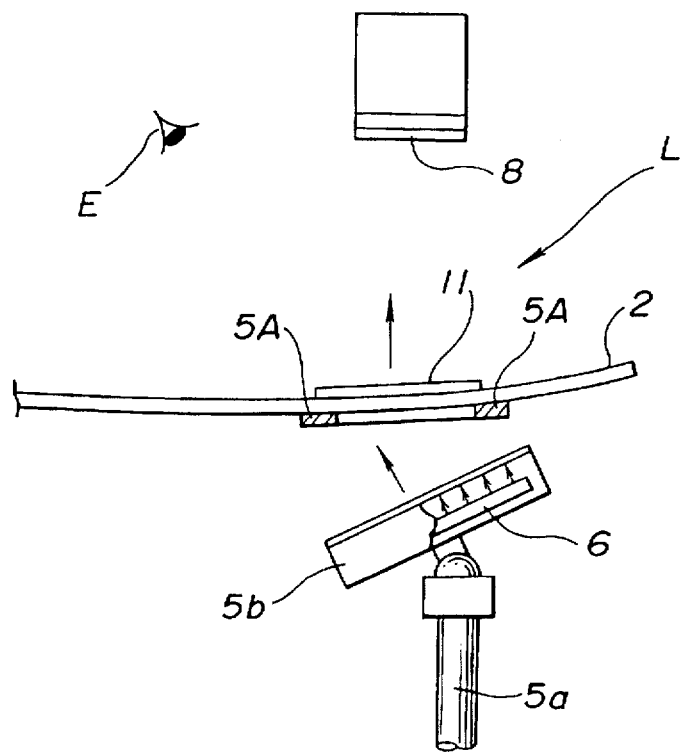
FIG. 9 is a fragmentary side view similar to FIG. 2 but showing an essential part of a third embodiment of the system according to the present invention.

FIG. 9 illustrates an essential part of a third embodiment of the location inspecting system L in accordance with the present invention, which is similar to the first embodiment with the exception that a hologram 11 is used in place of the polarization-direction changing film 1. In this embodiment, the hologram 11 is of the transmission type and prepared as follows: A photographic plate formed of a light-sensitive material such a photopolymer or gelatin dichromate is irradiated in two directions with laser beams to form interference fringes thereon, in such a manner as to make a reconstructed image under the condition of the reconstruction. Thereafter, the photographic plate is developed to thereby obtain the hologram 11 of the transmission type in a state of being fixedly mounted on a substrate (not shown).

The hologram 11 is stuck on the concave surface of an outboard-side transparent (glass) plate 2 of a rear windowpane of an automotive vehicle with an adhesive tape (not shown). The outboard-side transparent plate is curved in which the hologram 11 is stuck on the concave surface of the transparent plate 2. Thereafter, an inboard-side transparent (glass) plate (not shown) is stuck to the outboard-side transparent plate 2 with the intermediate film (not shown) which is formed of polyvinyl butyral or the like and located between the outboard-side transparent plate 1 and the inboard-side transparent plate. Then, a usual autoclave treatment is conducted on the above glass arrangement including the outboard-side and inboard-side transparent plates thereby accomplishing a laminating process thus forming the rear windowpane in which the hologram constitutes a so-called high mount stop lamp.

An inspection for location of the hologram 11 is accomplished before the above laminating process by using the location inspecting system L. The hologram 11 is to be located and stuck such that its peripheral edge is located at or brought into coincidence with a standard peripheral position S indicated by a dot-dash line in FIG. 3. However, in fact, it is difficult to accurately locate the hologram 11 at this standard position S, and therefore it is permitted that the peripheral edge of the hologram 11 is located between the outer permissible line SL and the inner permissible line SS as shown in FIG. 3. The outer permissible line SL is separate outward from the dot-dash line of the standard peripheral position S, for example, by 1 to several mm, while the inner permissible line SS is separate inward from the dot-dash line of the standard peripheral position S, for example, by 1 to several mm. It will be understood that the location of the stuck hologram 11 is judged to be suitable or accepted, in case that the hologram 11 is stuck such that the peripheral edge thereof is located between the outer permissible line SL and the inner permissible line SS.

The location inspecting system L of this embodiment is constructed and arranged in the same fashion as that of the first embodiment and therefore has a similar structure to that shown in FIGS. 1 and 2. The location inspecting system L includes the support rod 5a which is provided extending vertically upwardly from the mount table 3 and arranged to be vertically extensible and contractible. As shown in FIG. 9, the support mount 5b is pivotally connected through the universal joint J to the tip end of the support rod 5a. A rectangular frame-shaped inspection plate or film 5A is disposed on the support mount 5b. A reconstruction light source 6 such as a white light is disposed within the support mount 5b to emit light to the inspection plate 5A. The inspection plate 5A is to be tightly contactable to the convex surface of the transparent plate 2 at a position corresponding to the hologram 11 to be stuck on the concave or opposite surface of the transparent plate 2 as shown in FIG. 9. The inspection plate 5A of this embodiment is formed by being cut out from a black flat plate or film (not shown) for interrupting light, in a manner to have the rectangular frame-shape. The rectangular frame-shaped inspection plate 5 has a cross-sectional area which is the same in dimensions as the area (hatched area) defined between the lines SL, SS in FIG. 3. The inspection plate 5A is adhered on the surface of a transparent substrate (not shown) such as a glass sheet or a sheet of polyethylene terephthalate. Additionally, the video cameral 8 is disposed over the hologram 11.

A manner of inspection for location of the hologram 11 using the location inspecting system L will be discussed hereinafter also with reference to FIGS. 1 and 3.

The transparent plate 2 (such as a glass plate) to which the hologram 11 has been stuck is mounted on the support mounts 3b before accomplishing the laminating process, in which the vertical dimension of respective support rods 3a are so adjusted that the support mounts 3b are brought into tight contact with the convex surface of the transparent plate 2 having the curvature. Then, the peripheral edges of the transparent plate 2 are brought into contact with the stopper or stoppers 4 at the three support mounts 3b so that the transparent plate 2 is mounted at the predetermined position. At this time, the inspection plate 5 is also adjusted in height or the like in conformity with the curvature of the transparent plate 2.

Figure 11:
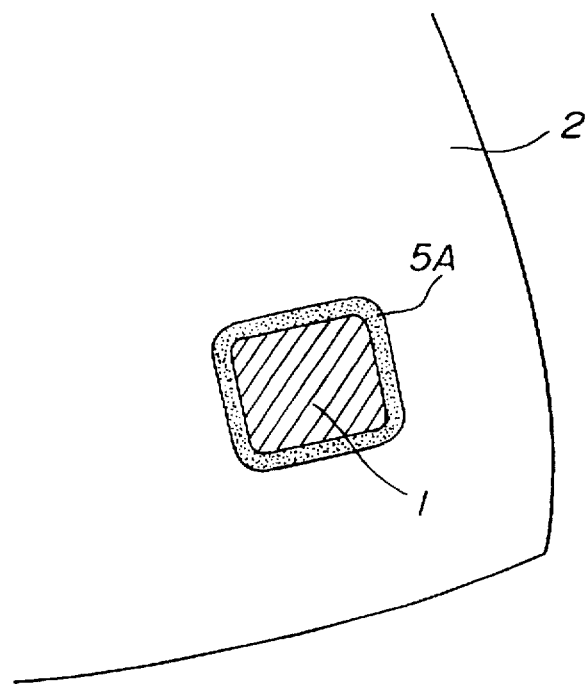
FIG. 11 is a fragmentary plan view of a transparent plate, showing the locational relationship of the optical film relative to the transparent plate in an operational mode, in the third embodiment of FIG. 9.

In this state, rays of light from the light source 6 are radiated to be incident on the hologram 11 and diffracted in the direction of the video camera 8. When the whole peripheral edge of the hologram 11 lies inside the hatched area in FIG. 3 or on the inspection plate 5A, an inner major part (hatched in FIG. 11) of the hologram 11 enclosed with the inner peripheral edge of the inspection plate 5A is seen, for example, green. Then, an observation of the side of the hologram 11 is made by the video camera 8. When the whole peripheral edge of the hologram 11 is mounted within the hatched area in FIG. 3 or over the inspection plate 5A, an optical image as shown in FIG. 11 is observed in which a light-interrupted part extends along the all four side sections of the hologram 11. As a result, a judgment is made as the location of the hologram 11 being accepted or within the permissible range.

Assume that the location of the hologram 11 deviates from the standard position S so that the whole peripheral edge of the hologram 11 is not within the hatched area in FIG. 3 or not over the inspection plate 5A. For example, a peripheral portion around the reconstructed section of the hologram 11 includes a light-transmitting part through which light from the light source 6 is directly transmitted, and a light-interrupting part at the left-side section of the optical image, and a light-interrupting part, and a hologram-reconstructing part at which reconstruction of the hologram 11 is made, at the right-side section of the optical image. In this case, the light-interrupting part does not extend along the whole peripheral edge of the hologram 11 and therefore a judgment is made as the location being rejected or not within the permissible range.

In this embodiment, when observation with human's eyes E is made on the side of the light source 6, light which has not been diffracted by the hologram 11 can be seen, for example, pink. Thus, the inspection of location of the stuck hologram 11 can be achieved also in this manner.

It will be appreciated that the video camera 8 is connected to an image processing device (not shown), in which signals representing light and dark areas of the optical image picked up by the video camera 8 is output to the image processing device thereby automatically judging as to whether the location of the stuck hologram 11 is within the permissible range or not.

Figure 10:
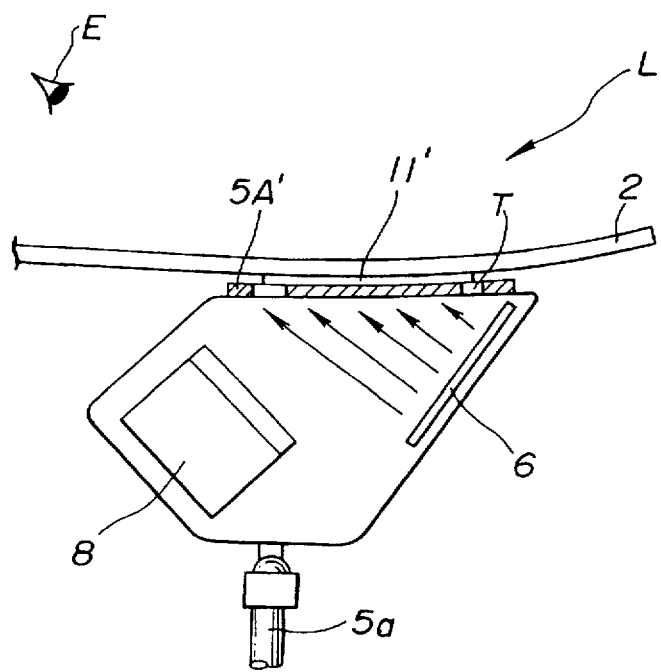
FIG. 10 is a fragmentary side view similar to FIG. 9 but showing an essential part of a modified example of the third embodiment of the system according to the present invention.

FIG. 10 shows a modified example of the third embodiment of the location inspection system L according to the present invention, which is similar to the third embodiment but arranged to accomplish the inspection for location of a reflection type hologram 11' to be stuck on the convex surface of the transparent plate 2. In this example, the inspection plate 5A' is produced by forming a cutout or through-hole T in a black flat plate or film (not shown) for interrupting light, the cutout T corresponding to the hatched area (defined between the permissible lines SL, SS) in FIG. 3 or to the permissible range for location of the stuck hologram 11'. In this embodiment, the video camera 8 is assembled with the light source 6 as a single unit (not identified) which is connected through the universal joint J to the tip end of the support rod 5a.

The manner of inspection for location of the hologram 11' using the location inspection system L of this embodiment will be discussed.

Figure 12:
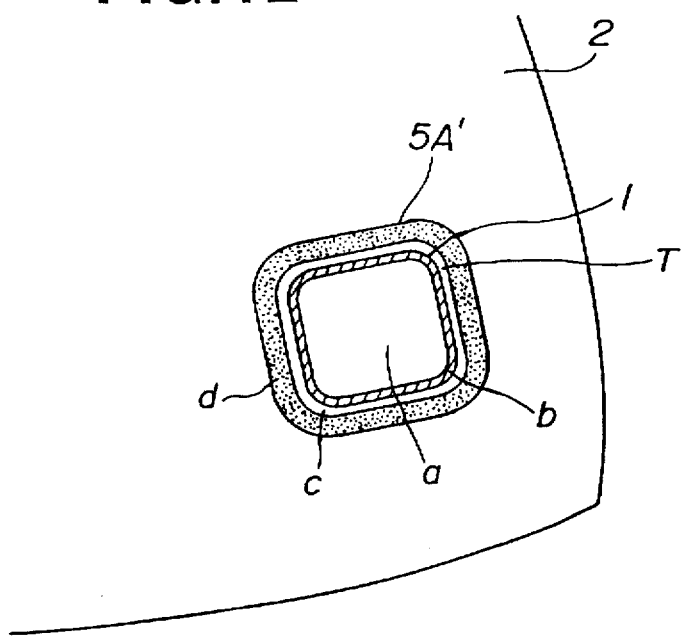
FIG. 12 is a fragmentary plan view similar to FIG. 11 but showing the locational relationship in an operational mode, in the modified example of FIG. 10.

The transparent plate 2 (such as glass plate) to which the hologram 11' is stuck is mounted on the support mounts 3b before accomplishing the laminating process, so that the transparent plate 2 is mounted at the predetermined position as shown in FIG. 1. In this state, rays of light from the reconstruction light source 6 is radiated onto the hologram 11' as shown in FIG. 10. When the whole peripheral edge of the hologram 11' is mounted on the cutout T or permissible range, an optical image as shown in FIG. 12 is observed by the video camera 8. The optical image in FIG. 12 includes an inner part a formed by interrupting light, a whole peripheral part b formed by diffracting, for example, green light into the direction of the video camera 8, an outside part c surrounding the whole peripheral part b, formed by passing light through the cutout T, and an outer-most part d formed by interrupting light with the outer peripheral section of the inspection plate 5A'. It will be understood that when the above optical image of FIG. 12 is observed, the location of the stuck hologram 11' is judged to be accepted.

Otherwise, the location of the stuck hologram 11' is judged to be rejected in case that the size of the hologram 11' is too large or the location of the stuck hologram 11' deviates from the permissible range so that a light-diffracted portion exists at the outer-most part d of the optical image, or in case that the size of the hologram 11' is too small so that no light-diffracted portion exists at the whole peripheral part b surrounding the inner part of the optical image.

In this example, when observation with human's eyes E is made at the upper side of the transparent plate 2, light which has not been diffracted by the hologram 11' can be seen, for example, pink at a position corresponding to the above-mentioned outside part c of the optical image of FIG. 12. Thus, the inspection of location of the stuck hologram 11 can be achieved also in this manner.

It will be appreciated in this example, that the inspection plate 5A' may be disposed in tight contact with the reflection type hologram 11' stuck on the upper surface of the transparent plate 2, in which the light source 6 is disposed over the transparent plate 2 so that light from the light source is diffracted upwardly by the hologram 11'. In this case, inspection for location of the stuck hologram 11' may accomplished by observing diffracted light at an upside of the transparent plate 2 while observing light which is not diffracted, at a downside of the transparent plate 2.

Although the transparent plate 2 used in the third embodiment has been shown and described as being the curved rear windowpane of the automotive vehicle, it will be appreciated that the transparent plate may be a windshield glass of other vehicles such as an airplane. Additionally, the transparent plate 2 may be replaced with a transparent plate forming part of a combiner of a head-up display system which is disposed separate from a rear windowpane, in which the transparent plate is made of not only glass but also transparent plastic such as polycarbonate or acrylic resin. Additionally, while the hologram 11 of the third embodiment has been shown and described as being used in a laminated glass, it will be understood that the hologram 11 may be stuck on a single plate glass.

In the above-discussed third embodiment, the inspection of the location of the hologram 11 has been shown and described as being carried out before the laminating process. This is preferable from such a view point as to reuse the glass plate provided with the hologram which is stuck at a position out of the permissible range. However, such an inspection may be carried out after the laminating process.

While the inspection plate 5A, 5A' has been shown and described as being formed of the black plate for interrupting light, it will be appreciated that the inspection plate may be formed of a gray filter (not shown) for reducing or dimming light. The inspection plate 5A, 5A' may be coated at its surface with a reflection-preventing film (not shown) so as to dim light to be reflected on the surface of the inspection plate, thereby facilitating optical discrimination thereof from a hologram section or the like.

While the white light has been shown and described as the light source 6, it will be understood that other light sources for emitting light having wavelengths for reconstruction of hologram image may be used in place of the white light. One of such light sources is a laser beam source for emitting laser beam having wavelengths for reconstruction of hologram image. However, the white light is preferable because it includes whole wavelengths. In this connection, it is preferable that the laser beam source is disposed close to the hologram in case of using the transmission type hologram, whereas it is disposed separate from the hologram in case of using the reflection type hologram because light is diffracted to the side of the laser beam source.

What is claimed is:

1. A method of inspecting a location of an optical film relative to a transparent plate at a predetermined position, comprising the following steps:

disposing an inspection plate to face a surface of said transparent plate and at a standard position at which said inspection plate includes an optically functioning section which has inner and outer peripheries, in section, defining therebetween an area corresponding to a permissible range for location of a peripheral edge of said optical film; and observing a locational relationship between the peripheral edge of said optical film and said area of said inspection plate under action of light reaching said optically functioning section so as to make a judgment as to whether the peripheral edge of said optical film is within said allowable range.

2. A system for inspecting a location of an optical film relative to a transparent plate, comprising:

mount means for supporting said transparent plate in conformity with a curvature of the transparent plate, said mount means including stoppers for locating said transparent plate;

an inspection plate disposed facing a surface of said transparent plate and located at a standard position at which said inspection plate includes an optically functioning section which has inner and outer peripheries, in section, defining therebetween an area corresponding to a permissible range for location of a peripheral edge of said optical film; and a light source for emitting light to reach said optically functioning section and said optical film, said optical film being located relative to a surface of said transparent plate.

3. A method of inspecting a location of a polarization-direction changing film relative to a transparent plate at a predetermined position, comprising the following steps:

disposing a first polarizing plate to face a first surface of said transparent plate and at a standard position at which said first polarizing plate has inner and outer peripheries, in section, defining therebetween an area corresponding to a permissible range for location of a peripheral edge of said polarization-direction changing film;

disposing a second polarizing plate to face a second surface of said transparent plate, in which said polarization-direction changing film is located relative to said transparent plate; and observing a locational relationship between the peripheral edge of said polarization-direction changing film and said area of said first polarizing plate through said second polarizing plate so as to make a judgment as to whether the peripheral edge of said polarization-direction changing film is within said allowable range.

4. A method as claimed in claim 3, further comprising the step of radiating rays of light on said first polarizing plate from a light source disposed facing the first surface of said transparent plate.

5. A system for inspecting a location of a polarization-direction changing film relative to a transparent plate, comprising:

mount means for supporting said transparent plate in conformity with a curvature of the transparent plate, said mount means including stoppers for locating said transparent plate;

a first polarizing plate disposed facing a first surface of said transparent plate and located at a standard position at which said first polarizing plate has inner and outer peripheries, in section, defining therebetween an area corresponding to a permissible range for location of a peripheral edge of said polarization-direction changing film;

a second polarizing plate disposed facing a second surface of said transparent plate, said polarization-direction changing film being located relative to said transparent plate; and a light source disposed facing the first surface of said transparent plate and located such that said first polarizing plate is positioned between said light source and said transparent plate.

6. A system as claimed in claim 5, further comprising means for observing a locational relationship between the peripheral edge of said polarization-direction changing film and said area of said first polarizing plate through said second polarization plate so as to make a judgment as to whether the peripheral edge of said polarization-direction changing film is within said allowable range.

7. A system as claimed in claim 5, wherein said mount means includes a plurality of vertically extending support rods for supporting said transparent plate, each support rod being controllable in length.

8. A method of sticking a polarization-direction changing film on a transparent plate at a predetermined position, comprising the following steps:

disposing a first polarizing plate to face a first surface of said transparent plate and at a standard position at which said first polarizing plate has inner and outer peripheries, in section, defining therebetween an area corresponding to a permissible range for location of a peripheral edge of said polarization-direction changing film;

disposing a second polarizing plate to face a second surface of said transparent plate, in which said polarization-direction changing film is located relative to said transparent plate;

moving said polarization-direction changing film toward a predetermined position corresponding to the standard position;

observing a locational relationship between the peripheral edge of said polarization-direction changing film and said area of said first polarizing plate through said second polarizing plate so as to make a judgment that the peripheral edge of said polarization-direction changing film is within said allowable range; and sticking said polarization-direction changing film on the second surface of said transparent plate at the standard position in response to said judgment.

9. A system for sticking a polarization-direction changing film on a transparent plate at a standard position, comprising:

a first polarizing plate disposed facing a first surface of said transparent plate and at a standard position at which said first polarizing plate has inner and outer peripheries, in section, defining therebetween an area corresponding to a permissible range for location of a peripheral edge of said polarization-direction changing film;

a second polarizing plate disposed facing a second surface of said transparent plate, said polarization-direction changing film being located relative to said transparent plate;

means for moving said polarization-direction changing film toward a predetermined position corresponding to the standard position;

means for observing a locational relationship between the peripheral edge of said polarization-direction changing film and said area of said first polarizing plate through said second polarizing plate so as to make a judgment that the peripheral edge of said polarization-direction changing film is within said allowable range; and means for sticking said polarization-direction changing film on the second surface of said transparent plate at the standard position in response to said judgment.

10. A method of inspecting a location of a hologram relative to a transparent plate at a predetermined position, comprising the following steps:

disposing an inspection plate to face a surface of said transparent plate and at a standard position at which said inspection plate includes a light-interrupting section which has inner and outer peripheries, in section, defining therebetween an area corresponding to a permissible range for location of a peripheral edge of said hologram, and a light-passing section other than said light-interrupting section;

radiating light from a light source onto said hologram through said area of said inspection plate, in which said hologram is located relative to a surface of said transparent plate; and observing a locational relationship between the peripheral edge of said hologram and said area of said inspection plate under action of light reaching said hologram upon passing through said light-passing section so as to make a judgment as to whether the peripheral edge of said hologram is within said allowable range.

11. A method of inspecting a location of a hologram relative to a transparent plate at a predetermined position, comprising the following steps:

disposing an inspection plate to face a surface of said transparent plate and at a standard position at which said inspection plate includes a light-passing section which has inner and outer peripheries, in section, defining therebetween an area corresponding to a permissible range for location of a peripheral edge of said hologram, and a light-interrupting section other than said light-passing section;

radiating light from a light source onto said hologram through said area of said inspection plate, in which said hologram is located relative to a surface of said transparent plate; and observing a locational relationship between the peripheral edge of said hologram and said area of said inspection plate under action of light reaching said hologram upon passing through said light-passing section so as to make a judgment as to whether the peripheral edge of said hologram is within said allowable range.

12. A system for inspecting a location of a hologram relative to a transparent plate, comprising:

mount means for supporting said transparent plate in conformity with a curvature of the transparent plate, said mount means including stoppers for locating said transparent plate;

an inspection plate disposed facing a surface of said transparent plate and located at a standard position at which said inspection plate includes an optically functioning section which has inner and outer peripheries, in section, defining therebetween an area corresponding to a permissible range for location of a peripheral edge of said hologram; and a light source for emitting light to reach said optically functioning section and said hologram, said hologram being located relative to a surface of said transparent plate.

13. A system as claimed in claim 12, further comprising means for observing a locational relationship between the peripheral edge of said hologram and said area of said inspection plate under action of light reaching said hologram upon passing through said inspection plate so as to make a judgment as to whether the peripheral edge of said hologram is within said allowable range.

14. A system as claimed in claim 12, wherein said mount means includes a plurality of vertically extending support rods for supporting said transparent plate, each support rod being controllable in length.

* * * * *